(12) United States Patent
Doerr et al.

(10) Patent No.: US 12,702,847 B2
(45) Date of Patent: Aug. 11, 2026

(54) IMPLANTABLE PULSE GENERATOR FOR TWO-STAGE THERAPY

(71) Applicant: BIOTRONIK SE & Co. KG, Berlin (DE)

(72) Inventors: Thomas Doerr, Berlin (DE); Ingo Weiss, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 261 days.

(21) Appl. No.: 17/420,306

(22) PCT Filed: Mar. 3, 2020

(86) PCT No.: PCT/EP2020/055520

§ 371 (c)(1),
(2) Date: Jul. 1, 2021

(87) PCT Pub. No.: WO2020/187555

PCT Pub. Date: Sep. 24, 2020

(65) Prior Publication Data

US 2022/0047878 A1 Feb. 17, 2022

(30) Foreign Application Priority Data

Mar. 20, 2019 (DE) ..................... 10 2019 107 117.8

(51) Int. Cl.
*A61N 1/00* (2006.01)
*A61N 1/39* (2006.01)

(52) U.S. Cl.
CPC ......... *A61N 1/3956* (2013.01); *A61N 1/3912* (2013.01); *A61N 1/395* (2013.01); *A61N 1/3981* (2013.01); *A61N 1/3987* (2013.01)

(58) Field of Classification Search
None
See application file for complete search history.

(56) References Cited

U.S. PATENT DOCUMENTS 5,036,850 A * 8/1991 Owens ............... A61N 1/36021 607/66
5,531,764 A * 7/1996 Adams ................ A61N 1/3956 607/15

(Continued)

FOREIGN PATENT DOCUMENTS

EP 2566578 B1 12/2017
EP 3342455 A1 7/2018

OTHER PUBLICATIONS

International Search Report (PCT/ISA/210) and Written Opinion (PCT/ISA/237) mailed on Jun. 26, 2020, by the European Patent Office as the International Searching Authority for International Application No. PCT/EP2020/055520.

*Primary Examiner* — William J Levicky
*Assistant Examiner* — Anant A Gupta
(74) *Attorney, Agent, or Firm* — Buchanan Ingersoll & Rooney PC

(57) ABSTRACT

An implantable medical device for generating electrical stimulations, wherein the medical device is embodied to generate and emit, during a first stimulation phase, at least one first stimulation that has a first amplitude by means of energy from an energy storage element, and wherein the medical device is embodied, during a second stimulation phase following the first stimulation phase, to generate and emit at least one second stimulation that has a second amplitude by means of energy from the energy storage element, wherein the energy storage element is charged at least prior to the generation of the at least one first stimulation and after the generation of the at least one first stimulation, and wherein the medical device is embodied not to completely discharge the energy storage element by (Continued)

generating the at least one first stimulation. The invention furthermore relates to a method for controlling such a device.

14 Claims, 3 Drawing Sheets

(56) References Cited

U.S. PATENT DOCUMENTS

| | | | | |
|---|---|---|---|---|
| 5,871,505 | A * | 2/1999 | Adams | A61N 1/3956 607/5 |
| 2002/0099413 | A1 * | 7/2002 | Mower | A61N 1/368 607/9 |
| 2003/0153953 | A1 * | 8/2003 | Park | A61N 1/36585 607/17 |
| 2004/0064154 | A1 * | 4/2004 | Norton | A61N 1/3975 607/7 |
| 2004/0073261 | A1 * | 4/2004 | Kroll | A61N 1/3918 607/5 |
| 2018/0140859 | A1 | 5/2018 | Meir | |

* cited by examiner

IMPLANTABLE PULSE GENERATOR FOR TWO-STAGE THERAPY

CROSS-REFERENCE TO RELATED APPLICATIONS

This application is the United States national phase under 35 U.S.C. § 371 of PCT International Patent Application No. PCT/EP2020/055520, filed on Mar. 3, 2020, which claims the benefit of German Patent Application No. 10 2019 107 117.8, filed on Mar. 20, 2019, the disclosures of which are hereby incorporated by reference herein in their entireties.

TECHNICAL FIELD

The present invention relates to an implantable medical device, in particular an implantable pulse generator, and to a method for controlling such a device.

BACKGROUND

As a rule, known implantable medical devices for anti-tachycardia therapies use high energy shocks or ATP (anti-tachycardia pacing). High energy shocks require not only a high amount of energy that must be provided by the battery or energy source of the device, and thus reduces the service life, in addition, due to the associated high voltages they may also impose a burden on, and even be damaging for, the organ undergoing therapy (electroporation). The drawbacks of ATP are that the location of the therapy may not be changed due to fixation of the electrode and the field of activity is very local. Furthermore, the voltages that may be achieved from the pace level are typically limited to 7.5 V, so that the efficacy is further limited by this.

European Patent No. 2 566 578 B1 describes a method for three-stage atrial cardioversion. The amplitude is successively reduced. A plurality of energy storage elements are used for the various stages.

European Publication No. 3 342 455 A1 relates to a multiphase ATP concept in which an increase in amplitude is described.

The present disclosure is directed toward overcoming one or more of the above-mentioned problems, though not necessarily limited to embodiments that do.

SUMMARY

Proceeding from the above, an underlying object of the present invention is to provide an implantable medical device or a method for controlling such a device, which device makes it possible to provide energy-saving stimulation and in particular stimulation that protects the organ (in particular against tachycardia).

At least this object is attained using an implantable medical device according to claim 1 and using a method according to claim 10. Advantageous embodiments of these aspects of the present invention are provided in the corresponding subordinate claims and are described in the following.

According to claim 1, an implantable medical device (e.g. a pulse generator) for generating electrical stimulations (in particular in the form of electrical stimulation pulses) is disclosed, wherein the medical device is embodied to generate and emit, during a first stimulation phase, at least one first stimulation that has a first amplitude by means of energy from an energy storage element, and wherein the medical device is embodied, during a second stimulation phase following the first stimulation phase, to generate and emit at least one second stimulation that has a second amplitude by means of energy from the energy storage element, wherein the energy storage element is charged at least prior to the generation of the at least one first stimulation and after the generation of the at least one first stimulation, and wherein the medical device is embodied not to completely discharge the energy storage element by generating the at least one first stimulation.

The inventive solution thus permits energy-saving and organ-protecting stimulation or therapy, wherein in particular, e.g. in the case of therapy for a tachycardia, if the first stimulation phase results in a lack of therapy success, a high energy therapy can be initiated immediately in the second stimulation phase.

According to one preferred embodiment, the implantable medical device is an implantable pulse generator. In this case the stimulation in question (first or second) is a stimulation pulse.

The inventive device may have a therapy unit for generating and emitting the stimulations or stimulation pulses by means of energy coming from the energy storage element. The therapy unit may be coupled to a patient's tissue to be provided therapy via a tissue interface (e.g. via one or a plurality of electrodes).

Moreover, according to one embodiment of the implantable medical device it is provided that the device is embodied for generating the at least one first and the at least one second stimulation such that the second amplitude is greater than the first amplitude.

Moreover, according to a first embodiment of the implantable medical device it is provided that the implantable medical device has an energy source and a charging circuit, the charging circuit being configured to charge the energy storage element up to a target energy level ($E_z$) by means of the energy source.

Moreover, according to one embodiment of the implantable medical device it is provided that the implantable medical device has a control unit, the control unit being configured to initiate the generation and emission of at least a first stimulation when charging the energy storage element before the energy level ($E_c$) of the energy storage element has achieved the target energy level.

Moreover, according to one embodiment of the implantable medical device it is provided that the control unit is configured to initiate the generation and emission of the at least one second stimulation only the target energy level has been achieved during charging of the energy storage element.

Moreover, according to one embodiment of the implantable medical device it is provided that the implantable medical device has a detection unit that is embodied to detect events or signals from a tissue or organ stimulated by means of the stimulations.

Moreover, according to one embodiment of the implantable medical device it is provided that the control unit is configured to terminate the first stimulation phase and to initiate the generation and emission of the at least one second stimulation during the second stimulation phase when one or a plurality of detected events satisfy a predefined criterion.

In this way it is possible in particular to determine, using the criterion, whether the at least one first stimulation already represents a therapy success, wherein in particular the at least one second stimulation is generated and emitted if the at least one first stimulation was not successful.

Moreover, according to one embodiment of the implantable medical device it is provided that the energy of the at least one first stimulation or the total energy of a plurality of first stimulations in the first stimulation phase is less than the energy of the at least one second stimulation or is less than the total energy of a plurality of second stimulations in the second stimulation phase.

The energy of the at least one first stimulation or the total energy of the plurality of first stimulations is preferably less than 50% of the energy of the at least one second stimulation or is less than 50% of the total energy of the plurality of second stimulations.

Moreover, according to one embodiment of the implantable medical device it is provided that the at least one second stimulation is designed for defibrillation of a patient's heart.

According to one embodiment of the medical device it is furthermore provided that the implantable medical device has implantable electrodes, wherein the device is embodied to feed the first and second stimulations (in particular stimulation pulses) galvanically via the electrodes into a patient's or person's tissue or organ that is to be provided therapy.

According to one alternative embodiment of the implantable medical device it is provided that the device is embodied to radiate the first and second stimulations (in particular stimulation pulses) in the form of electromagnetic radiation into a patient's or person's tissue or organ that is to be provided therapy.

Moreover, according to one embodiment of the implantable medical device it is provided that the control unit of the device is configured for terminating the first stimulating phase and continuing with the second stimulation phase when a predefined or programmed quantity of energy of the at least one first stimulation or plurality of first stimulations (preferably less than 50% of the energy provided for the second stimulation phase) has been used without therapy success.

Moreover, according to one embodiment of the implantable medical device it is provided that the control unit is configured to terminate the first stimulation phase and continue with the second stimulation phase if the first stimulation phase has not achieved therapy success or the aforesaid criterion has not been satisfied upon achieving a predefined or programmed voltage or upon achieving a predefined or programmed current of the at least one first stimulation or of one or a plurality of further first stimulations.

Moreover, according to one embodiment of the implantable medical device it is provided that the control unit is configured to terminate the first stimulation phase and to continue with the second stimulation phase if the first stimulation phase has not demonstrated any therapy success or if the aforesaid criterion has not been satisfied over a predefined or programmed period.

Moreover, according to one embodiment of the implantable medical device it is provided that the device has a learning unit that is embodied to determine a correlation between a therapy success of the first stimulation phase and a parameter set of the first stimulation phase and/or a correlation between a therapy success of the second stimulation phase and a parameter set of the second stimulation phase. In this correlation, therapy success is detected and assessed as one or a plurality of parameters that describe the excitation status of the tissue undergoing therapy and, in the case of success, a corresponding tissue reaction can be derived, such as, e.g. generation of a tissue excitation, cancellation of a tissue excitation, contraction or relaxation of a muscular tissue structure, recording of a so-called evoked potential, the intentional change in a cardiac rhythm and/or comparable excitation conditions of the tissue. The respective parameter sets for the first and second stimulation phases may include, e.g., parameters such as amplitudes, pulse widths, signal shape parameters, signal rise and/or signal decline speeds and timing pulses, such as the temporal coupling of pulse emissions to synchronization events.

Moreover, according to one embodiment of the implantable medical device it is provided that the learning unit has an information storage element and optionally a statistics unit.

Moreover, according to one embodiment of the implantable medical device it is provided that the learning unit is configured for ordering the parameter sets in the sequence of the therapy success achieved therewith or for ordering the parameter sets in the sequence of the probability of achieving the desired therapy success.

Moreover, according to one embodiment of the implantable medical device it is provided that the learning unit is configured for adjusting the sequence using detected data, in particular continuously or repeatedly (tracking).

Moreover, according to one embodiment of the implantable medical device it is provided that the control unit is configured to start the first stimulation phase with a parameter set for a stimulation, the parameter set promising the highest therapy success according to the learning unit.

Moreover, according to one embodiment of the implantable medical device it is provided that the first stimulation phase is divided into subphases, wherein according to one embodiment the device is configured to start a first subphase with a parameter set for a stimulation, the parameter set promising the highest therapy success according to the learning unit, followed by a programmable number of additional subphases with parameters sets in the sequence of decreasing chances of success.

Moreover, according to one embodiment of the implantable medical device it is provided that each stimulation in the first stimulation phase and/or in the second stimulation phase is a stimulation pulse. The characterizing parameters for such a stimulation pulse are in particular: amplitude (voltage or current), polarity, pulse width, and interval until the next stimulation pulse.

Moreover, according to one embodiment of the implantable medical device it is provided that the device is configured to start a first subphase of the subphases with a parameter set that was successful in the most recent past or in a defined past time period, regardless of the previous statistical ranking.

Moreover, according to one embodiment of the implantable medical device it is provided that the device is configured to emit each stimulation (in particular each stimulation pulse) in a time-controlled manner.

Moreover, according to one embodiment of the implantable medical device it is provided that the device is embodied to emit each stimulation (in particular each stimulation pulse) in an amplitude-controlled manner (e.g. with respect to voltage, current, or quantity of energy).

Moreover, according to one embodiment of the implantable medical device it is provided that the device is configured such that the charge removed from the energy storage element per stimulation pulse is less than or equal to a charge amount that is recharged by means of the charging circuit in a period up to the next stimulation pulse. I.e., in particular in other words that, despite a charge being taken repeatedly from the energy storage element, the peak voltage of the stimulation pulse increases, or at least remains constant, from pulse to pulse.

Moreover, according to one embodiment of the implantable medical device it is provided that the device is configured such that each stimulation pulse is emitted as a function of an event in a patient's or person's tissue or organ that was detected by means of the detection unit.

Moreover, according to one embodiment of the implantable medical device it is provided that the device has a telemetry unit.

Moreover, according to one embodiment of the implantable medical device it is provided that the device is embodied to obtain parameters for the specific stimulation (or the specific stimulation pulse) via the telemetry unit.

Moreover, according to one embodiment of the implantable medical device it is provided that at least some of the stimulation phases or the individual stimulations or stimulation pulses of the stimulation phases may be triggered from outside via the telemetry unit.

Moreover, according to one embodiment of the implantable medical device it is provided that the charging circuit has a charging speed of at least 1 J/s, preferably of at least 5 J/s.

Moreover, according to one embodiment of the implantable medical device it is provided that the charging circuit has an adjustable charging speed.

Moreover, according to one embodiment of the implantable medical device it is provided that the charging speed of the charging circuit varies, wherein in particular a charging speed during the first stimulation phase differs from a charging speed of the second stimulation phase.

Moreover, according to one embodiment of the implantable medical device it is provided that the charging circuit is configured to change the charging speed in a time-controlled, voltage-controlled, or energy-controlled manner (e.g. if a specific threshold is exceeded).

Moreover, according to one embodiment of the implantable medical device it is provided that the therapy unit has a tissue interface via which energy of each stimulation or of each stimulation pulse may be coupled into a tissue to undergo therapy.

Moreover, according to one embodiment of the implantable medical device it is provided that the device is embodied for antitachycardia stimulation of the heart or of the chambers or of the atria of the heart.

Moreover, according to one embodiment of the implantable medical device it is provided that the device is an implantable pulse generator, in particular an implantable intracardiac or subcutaneous cardioverter defibrillator.

Moreover, according to one embodiment of the implantable medical device it is provided that the tissue interface is formed by electrically conductive electrode poles.

Another aspect of the present invention relates to a method for controlling an implantable medical device, in particular an implantable medical device according to any of the preceding claims, having the steps: emitting at least one first stimulation from an energy storage element of the device (e.g. pulse generator) during a first stimulation phase, the at least one first stimulation having a first amplitude; emitting at least one second stimulation from the same energy storage element during a second stimulation phase following the first stimulation phase, the at least one second stimulation having a second amplitude, wherein the energy storage element is charged at least prior to and following the emission of the at least one first stimulation, and wherein the energy storage element is not completely discharged by the at least one first stimulation.

Each stimulation is preferably a stimulation pulse. Moreover, the inventive medical device is preferably an implantable pulse generator (see above, also).

According to one embodiment of the inventive method it is provided that the second amplitude is greater than the first amplitude.

Moreover, according to one embodiment of the inventive method, it is provided that the energy storage element is charged up to a target energy level.

Moreover, according to one embodiment of the inventive method it is provided that the at least one first stimulation is emitted before the energy level ($E_c$) of the energy storage element has achieved the target energy level.

Moreover, according to one embodiment of the inventive method it is provided that the at least one second stimulation is not emitted until the target energy level has been achieved during charging of the energy storage element.

Moreover, according to one embodiment of the inventive method it is provided that events or signals from tissue to be stimulated by means of the stimulations are detected by means of the device (in particular a pulse generator), the at least one second stimulation being emitted when at least one detected event satisfies a predefined criterion (see above, also).

According to another embodiment of the inventive method it is provided that the energy of the at least one first stimulation or the total energy of a plurality of first stimulations in the first stimulation phase is less than the energy of the at least one second stimulation or is less than the total energy of a plurality of second stimulations in the second stimulation phase. The energy of the at least one first stimulation or the total energy of the plurality of first stimulations is preferably less than 50% of the energy of the at least one second stimulation or less than 50% of the total energy of the at least second stimulations.

Moreover, according to one embodiment of the inventive method it is provided that defibrillation of a patient's heart is performed by means of the at least one second stimulation.

Moreover, according to one embodiment of the inventive method it is provided that the first and second stimulations (in particular stimulation pulses) are emitted or fed galvanically into a patient's or person's tissue via electrodes.

Moreover, according to one alternative embodiment of the inventive method it is provided that the first and second stimulations (in particular stimulation pulses) are radiated in the form of electromagnetic radiation into a patient's or person's tissue or organ that is to be provided therapy.

Moreover, according to one embodiment of the inventive method it is provided that the first stimulation phase is terminated and the method is continued with the second stimulation phase when a predefined or programmed quantity of energy of the at least one first stimulation or a plurality of first stimulations (preferably less than 50% of the energy provided for the second stimulation phase) has been used without therapy success.

Moreover, according to one embodiment of the inventive method it is provided that the first stimulation phase is terminated and the method is continued with the second stimulation phase if the first stimulation phase, upon achieving a predefined or programmed voltage or upon attaining a predefined or programmed current of the at least one first stimulation or of one or a plurality of further first stimulations, has not achieved therapy success or the aforesaid criterion has not been satisfied.

According to another embodiment of the inventive method it is provided that the first stimulation phase is terminated and the method is continued with the second stimulation phase if the first stimulation phase has not demonstrated any therapy success or the aforesaid criterion has not been satisfied over a predefined or programed period of time.

Moreover, according to one embodiment of the inventive method it is provided that a correlation is found between a therapy success of the first stimulation phase and a parameter set of the first stimulation phase and/or a correlation is found between a therapy success of the second stimulation phase and a parameter set of the second stimulation phase. In this correlation, therapy success is detected and assessed as one or a plurality of parameters that describe the excitation status of the tissue undergoing therapy and in the case of success a corresponding tissue reaction can be derived, such as e.g. the generation of tissue excitation, the cancellation of a tissue excitation, contraction or relaxation of a muscular tissue structure, recording of a so-called evoked potential, the intentional change in a cardiac rhythm and/or comparable excitation conditions of the tissue. The specific parameter sets for the first and second stimulation phases may include, e.g., parameters such as amplitudes, pulse widths, signal forming parameters, signal shape parameters, signal rise and/or signal decline speeds and timing pulses, such as the temporal coupling of pulse emissions to synchronization events.

Moreover, according to one embodiment of the inventive method it is provided that the parameter sets are automatically ordered in the sequence of the therapy success achieved therewith, or that the parameter sets are automatically ordered in the sequence of the probability of achieving the desired therapy success.

Moreover, according to one embodiment of the inventive method it is provided that the sequence is adjusted using detected data, in particular is continuously or repeatedly adjusted (tracking).

Moreover, according to one embodiment of the inventive method it is provided to start the first stimulation phase with a parameter set for a stimulation, the set promising the highest therapy success according to the learning unit.

Moreover, according to one embodiment of the inventive method it is provided that the first stimulation phase is divided into subphases, wherein according to one embodiment a first subphase is started with a parameter set for a stimulation, the parameter set promising the highest therapy success according to the learning unit, followed by a programmable number of additional subphases with parameters sets in the sequence of decreasing chances of success.

Moreover, according to one embodiment of the inventive method it is provided that each stimulation in the first stimulation phases and/or in the second stimulation phase is a stimulation pulse. The characterizing parameters for one such stimulation pulse are again in particular: amplitude (voltage or current), polarity, pulse width, and interval to next stimulation pulse (see above, also).

According to another embodiment of the inventive method it is provided that a first subphase of the subphases is started with a parameter set that was successful in the most recent past or in a defined past time period, regardless of the previous statistical ranking.

Moreover, according to one embodiment of the inventive method it is provided that each stimulation (in particular each stimulation pulse) is emitted in a time-controlled manner.

Moreover, according to one embodiment of the inventive method it is provided that each stimulation (in particular each stimulation pulse) is emitted in an amplitude-controlled manner (e.g. with respect to voltage, current, or quantity of energy).

Moreover, according to one embodiment of the inventive method it is provided that the charge removed from the energy storage element per stimulation pulse is less than or equal to a charge amount that is recharged by means of the charging circuit in a period up to the next stimulation pulse.

Moreover, according to one embodiment of the inventive method it is provided that each stimulation pulse is emitted as a function of an event in a patient's or person's tissue or organ that was detected by means of the detection unit.

Moreover, according to one embodiment of the inventive method it is provided that parameters for each stimulation (or each stimulation pulse) are transmitted to the implantable medical device from outside via a telemetry unit.

According to another embodiment of the inventive method it is provided that at least some of the stimulation phases or the individual stimulations or stimulation pulses of the stimulation phases are triggered from outside via the telemetry unit of the implantable medical device.

Moreover, according to one embodiment of the inventive method it is provided that the energy storage element is charged at a charging speed of at least 1 J/s, preferably at least 5 J/s.

Moreover, according to one embodiment of the inventive method it is provided that the charging speed is adjustable or adjusted.

According to one embodiment of the inventive method it is preferably provided that the charging speed is varied so that in particular a charging speed during the first stimulation phase differs from a charging speed during the second stimulation phase.

According to another embodiment of the inventive method it is provided that the charging speed is changed or varied in a time-controlled, voltage-controlled, or energy-controlled manner (e.g. when a specific threshold is exceeded).

Moreover, according to one embodiment of the inventive method it is provided that the energy of each stimulation or of each stimulation pulse is coupled via a tissue interface into a tissue to undergo therapy, the tissue interface being in particular electrically conductive electrode poles.

Additionally, according to another embodiment of the inventive method it is provided that the stimulations represent antitachycardia stimulation of the heart or ventricles and/or atria of the heart.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Embodiments and features of the present invention shall be explained in the following using the figures.

DETAILED DESCRIPTION

Figure 1:
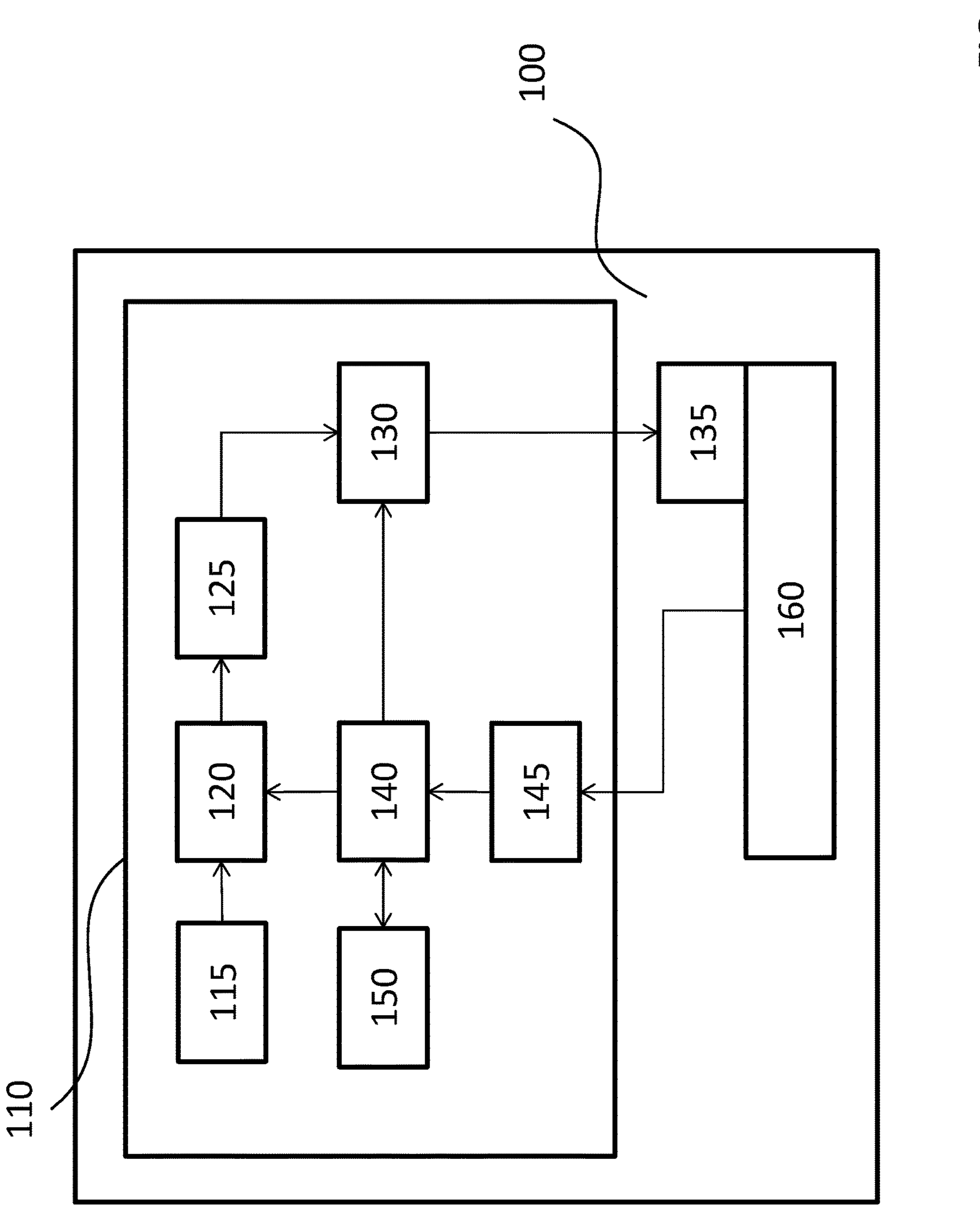
FIG. 1 depicts one embodiment of the inventive implantable medical device.
Figure 2:
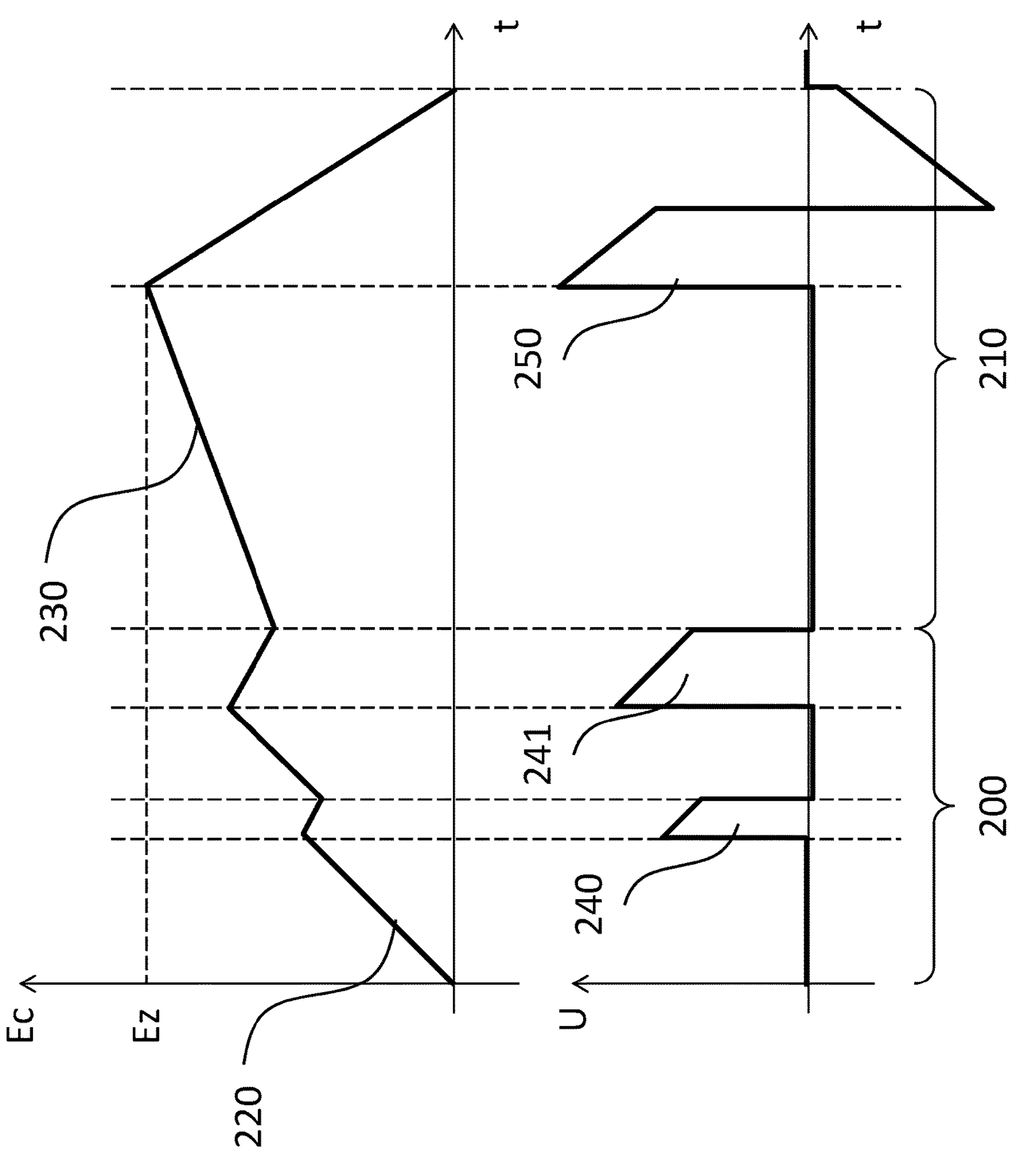
FIG. 2 depicts a temporal curve for a first and a second stimulation phase performed with the device.
Figure 3:
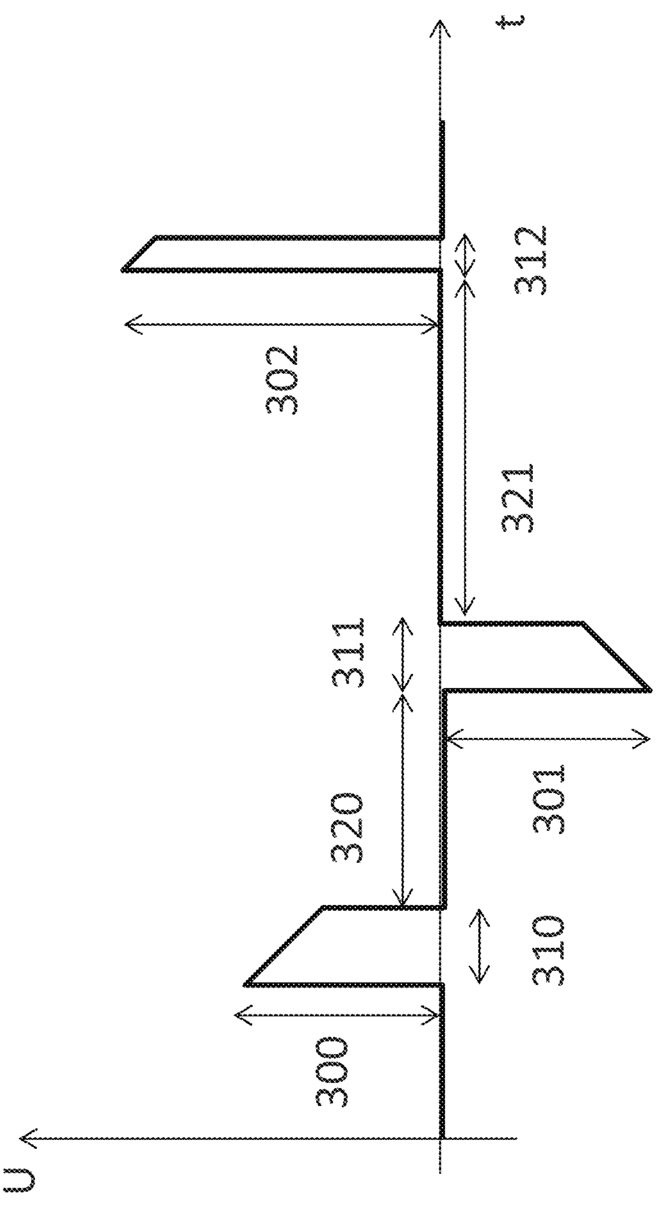
FIG. 3 depicts typical parameters of stimulation pulses that are generated by means of the inventive device.

In conjunction with FIGS. 2 and 3, FIG. 1 depicts an embodiment of an inventive medical device 110 for generating electrical stimulations, wherein the device 110 is implantable in a body 100 of a person or patient, and wherein the medical device 110 is preferably embodied to generate and emit into tissue 160 or an organ 160 of the body 100, during a first stimulation phase 200, at least one first stimulation 240 (optionally another first stimulation 241) that has a first amplitude by means of energy from an energy storage element 125, and wherein the medical device 110 is furthermore embodied, during a second stimulation phase 210 following the first stimulation phase 200, to generate and emit into the tissue/organ 160 at least one second stimulation 250 that has a second amplitude by means of energy from the energy storage element 125, wherein the energy storage element 125 is charged at least prior to the generation of the at least one first stimulation 240 and after the generation of the at least one first stimulation 240, and wherein the medical device is embodied not to completely discharge the energy storage element 125 by the generation of the at least one first stimulation 240.

The present invention thus permits a two-stage, e.g. antitachycardia, therapy, wherein in particular during the charging of the energy storage element 125 for the second therapy or stimulation phase 210 a first stimulation 240 is emitted that is supplied from the same energy storage element 125 and preferably uses the same electrodes 135 as the subsequent second stimulation/therapy 250. The first stimulation phase 200 is characterized in that it typically acts increasingly more aggressively as voltage increases in the energy storage element 125 in preparation for the second stimulation phase and there is a high probability of success for ending the tachycardia during this first stimulation phase 200. If this is not the case, the second stimulation phase 210 takes place. The first stimulation phase 200 is also characterized in that it requires significantly less energy and is more protective of the organ.

In detail, the device 110 according to FIG. 1 may be designed, e.g. as an implantable pulse generator 110 that emits the individual stimulations 240, 241, 250 in the form of stimulation pulses. According to one embodiment, the pulse generator or the device 110 has an energy source 115 (e.g. battery), an energy storage element 125, a charging circuit 120, a control unit 140, and a detection unit 145 that registers events from the tissue 160. The device 110 furthermore preferably has a therapy unit 130 for generating the stimulations/stimulation pulses, the therapy unit 130 emitting the stimulations/stimulation pulses into the tissue 160 via a tissue interface 135 to the tissue 160 to be provided therapy (e.g. in the form of electrodes). Moreover, the device 110 may have a telemetry unit 150.

FIG. 2 depicts the temporal curve of a typical inventive realization of the two-phase therapy comprising a first stimulation phase 200 and a second stimulation phase 210. As long as the energy level in the energy storage element 125 is below the target energy level $E_z$, charging occurs at the charging speed 220. The stimulation pulses 240 and 241 are emitted during the course of this first stimulation phase 200. A criterion detected by the detection unit 145 preferably introduces the second stimulation phase 210. In doing so, where necessary charging must continue up to the target energy level $E_z$, which here optionally occurs at a different charging speed 230. Once the target energy level has been achieved, the at least one stimulation pulse 250 (optionally a plurality of second stimulation pulses) of the second stimulation phase is emitted.

FIG. 3 provides an exemplary depiction of the typical parameters of the stimulation pulses 240, 241, 250 the inventive device 110 generates according to one embodiment. In the example shown, these are changing polarity (e.g. of the first stimulation phase 200), the amplitudes 300, 301, and 302, the pulse widths 310, 311, and 312, and the intervals 320 and 321 until the next stimulation pulse.

The inventive solution reaches greater areas in the organ to be provided therapy just in the first stimulation phase 200 than is possible using ATP, and specifically in particular due to a far field effect and the higher possible voltages compared to conventional pacing stages. The far field effect in this context describes the effect that a stimulation pulse generates excitation fronts in tissue areas farther way from the stimulation site. The far field effect may be amplified by overlaying stimulation pulses. One advantage of the stimulation effect in the far field effect is the more homogeneous distribution of the stimulation energy in the tissue. Thus the tissue in the far field is stimulated without points of higher energy density, so that it is possible to prevent tissue damage. The inventive solution makes possible a progressive increase in the effect not only by timing (as for conventional ATP, ramping, coupling, etc.), but also in particular due to the increasing amplitudes of the stimulation pulses 240, 241, etc. Due to a smaller duty cycle and lower peak voltages, this first therapy stage also requires significantly less energy than a high energy therapy; however, for safety reasons high energy therapy is also possible immediately in principle.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. An implantable medical device for generating electrical stimulations, wherein the medical device is embodied to generate and emit, a first therapy treatment via a first stimulation phase, wherein at least one first stimulation that has a first amplitude is generated by means of energy from an energy storage element, and a second therapy treatment via a second stimulation phase following the first stimulation phase when it is determined that the at least one first stimulation does not result in a therapy treatment success, wherein at least one second stimulation that has a second amplitude is generated by means of energy from the energy storage element, wherein the energy storage element is charged prior to the generation of the at least one first stimulation and after the generation of the at least one first stimulation but before generation of the at least one second stimulation, wherein the medical device is embodied not to completely discharge the energy storage element by generating the at least one first stimulation, wherein the energy of the at least one first stimulation is less than the energy of the at least one second stimulation, or the total energy of a plurality of first stimulations in the first stimulation phase is less than the total energy of a plurality of second stimulations in the second stimulation phase, and wherein the implantable medical device includes a control unit configured for terminating the first stimulation phase and continuing with the second stimulation phase when a predefined quantity of energy of the at least one first stimulation has been used without therapy success and/or when the first stimulation phase has not demonstrated any therapy success over a predefined or programmed period, wherein the first stimulation phase is divided into subphases with a parameter set for a highest therapy success in a first subphase followed by additional subphases with parameters sets in the sequence of decreasing chances of success.

2. The implantable medical device according to claim 1, wherein the second amplitude is greater than the first amplitude.

3. The implantable medical device according to claim 1, wherein the implantable medical device has an energy source and a charging circuit, the charging circuit being configured to charge the energy storage element up to a target energy level ($E_z$) by means of the energy source.

4. The implantable medical device according to claim 3, wherein the control unit is configured to initiate the generation and emission of the at least one first stimulation when charging the energy storage element before an energy level ($E_c$) of the energy storage element has achieved the target energy level ($E_z$).

5. The implantable medical device according to claim 4, wherein the control device is configured to initiate the generation and emission of the at least one second stimulation only if the target energy level ($E_z$) has been achieved during charging of the energy storage element.

6. The implantable medical device according to claim 1, wherein the implantable medical device has a detection unit that is embodied to detect events from a tissue stimulated by means of the stimulations.

7. The implantable medical device according to claim 6, wherein the control unit is configured to initiate the generation and emission of the at least one second stimulation when one or a plurality of detected events satisfy a predefined criterion.

8. The implantable medical device according to claim 1, wherein the at least one second stimulation is designed for defibrillation of a patient's heart.

9. A method for controlling an implantable medical device, in particular an implantable medical device according to claim 1, comprising the steps:

Emitting, via a first therapy treatment, at least one first stimulation from an energy storage element of the device during a first stimulation phase, the at least one first stimulation having a first amplitude, wherein the at least one first stimulation phase is divided into subphases with a parameter set for a highest therapy success in a first subphase followed by additional subphases with parameters sets in the sequence of decreasing chances of success, Emitting, via a second therapy treatment, at least one second stimulation from the same energy storage element during a second stimulation phase following the first stimulation phase when it is determined that the at least one first stimulation does not result in a therapy treatment success, the at least one second stimulation having a second amplitude, wherein the energy storage element is charged prior to and following the emission of the at least one first stimulation but before the emission of the at least one second stimulation, and wherein the energy storage element is not completely discharged by the at least one first stimulation, and Terminating the first stimulation phase and continuing with the second stimulation phase when a predefined quantity of energy of the at least one first stimulation has been used without therapy success and/or when the first stimulation phase has not demonstrated any therapy success over a predefined or programmed period.

10. The method according to claim 9, wherein the second amplitude is greater than the first amplitude.

11. The method according to claim 9, wherein the energy storage element is charged up to a target energy level ($E_z$).

12. The method according to claim 11, wherein the at least one first stimulation is emitted before an energy level ($E_c$) of the energy storage element has achieved the target energy level ($E_z$).

13. The method according to claim 12, wherein the at least one second stimulation is not emitted until the target energy level ($E_z$) has been achieved during charging of the energy storage element.

14. The method according to claim 9, wherein events from tissue to be stimulated by means of the stimulations are detected by means of the device, the at least one second stimulation being emitted when at least one detected event satisfies a predefined criterion.

* * * * *